(12) United States Patent
Ishihara et al.

(10) Patent No.: US 6,592,818 B2  
(45) Date of Patent: Jul. 15, 2003

(54) AUTOMATIC ANALYZER

(75) Inventors: Naruhito Ishihara, Sagamihara (JP); Tetsufumi Matsumoto, Fujisawa (JP)

(73) Assignee: Tosoh Corporation, Shinnanyo (JP)

( * ) Notice: Subject to any disclaimer, the term of this patent is extended or adjusted under 35 U.S.C. 154(b) by 0 days.

(21) Appl. No.: 10/199,126

(22) Filed: Jul. 22, 2002

(65) Prior Publication Data

US 2002/0182108 A1 Dec. 5, 2002

Related U.S. Application Data (62) Division of application No. 09/534,627, filed on Mar. 27, 2000, now Pat. No. 6,461,570.

(30) Foreign Application Priority Data

Mar. 25, 1999 (JP) ............................................. 11-081223  
Mar. 25, 1999 (JP) ............................................. 11-081224

(51) Int. Cl.[7] ........................ G01N 35/00; G01N 35/02  
(52) U.S. Cl. ........................ 422/62; 422/63; 422/65; 422/67; 436/43; 436/47; 702/31  
(58) Field of Search ............................... 422/62, 63, 65, 422/67; 436/43, 47; 702/31

(56) References Cited

U.S. PATENT DOCUMENTS 3,985,508 A   10/1976   Williams  
4,078,895 A    3/1978   Moran  
5,178,834 A    1/1993   Kagayama et al.

FOREIGN PATENT DOCUMENTS

JP   3-51762   3/1991  
JP   3-58668   9/1991

*Primary Examiner*—John Kim  
(74) *Attorney, Agent, or Firm*—Oblon, Spivak, McClelland, Maier & Neustadt, P.C.

(57) ABSTRACT

An automatic analyzer which includes a storage means which stores test order information, a first identification means which reads sample identification information, a work list preparing means which prepares a work list on the basis of the sample identification information, a loading order determination means which determines the order in which sample cups and reaction cups are loaded from the work list, a second identification means which automatically reads specification component information and a collating means which compares the specific component information with the work list.

2 Claims, 4 Drawing Sheets

1: TEST ORDER INFORMATION  
2: REGISTRATION MEANS  
3: SAMPLE CUP  
4: SAMPLE IDENTIFICATION INFORMATION  
5: FIRST IDENTIFICATION MEANS  
6: WORK LIST PREPARING MEANS  
7: DISPLAY  
10: CONVEYOR  
11: REACTION AND DETECTION SITE  
12: COLLATING MEANS  
13: OUTPUT DEVICE  
*1: SAMPLE IDENTIFICATION INFORMATION  
*2: SPECIFIC COMPONENT INFORMATION

1: TEST ORDER INFORMATION
2: REGISTRATION MEANS
3: SAMPLE CUP
4: SAMPLE IDENTIFICATION INFORMATION
5: FIRST IDENTIFICATION MEANS
6: WORK LIST PREPARING MEANS
7: DISPLAY
10: CONVEYOR
11: REACTION AND DETECTION SITE
12: COLLATING MEANS
13: OUTPUT DEVICE
*1: SAMPLE IDENTIFICATION INFORMATION
*2: SPECIFIC COMPONENT INFORMATION

FIG. 4

AUTOMATIC ANALYZER

This application is a Division of application Ser. No. 09/534,627 filed on Mar. 27, 2000 now U.S. Pat. No. 6,461,570.

The present invention relates to an analyzer for trace component analysis of samples such as blood, serum, plasma or urine, especially an automatic analyzer for biochemical or immunological trace component analysis of such samples.

In the field of clinical diagnostics, analyzers are used widely for detection and determination of specific components in blood, serum, plasma or urea samples from examinees to provide useful data for diagnoses of diseases. Among analyzers, multichannel biochemical analyzers determine saccharides, lipids and proteins by using enzymatic reactions and chemical reactions, and multichannel immunological analyzers determine hormones and tumor markers by using specific interaction between antigens and antibodies. These analyzers usually perform biochemical reactions and immunological reactions in individual disposable reaction cups to avoid contamination among samples or reaction liquids. Prefilled reaction cups already containing a reagent for a specific component in samples to be measured are usually disposable too.

Instrumental analyses as mentioned above usually cover more than one specific component in a sample to make good use of samples from examinees or to secure more accurate diagnosis based on multiple components.

To speed up and facilitate numerous operations necessary for determination of multiple specific components in samples, automatic analyzers have been used routinely. Typical automatic analyzers in present use add given amounts of samples to prefilled reaction cups already containing reagents for measurement of specific components and, optionally, incubate and wash the reaction cups for determination of various specific components in each sample.

Further, a full-automatic biochemical analyzer equipped with an automatic loader which selects a prefilled reaction cup containing a reagent proper for a specific component and places it on a tray on a conveyer (JP-B-3-58666) and an automatic analyzer with a conveyer which automates operations from conveyance of a sample cup to output of the results once the operator places the sample cup and the reaction cup (JP-A-3-51762) are known.

Analyzers like these usually sucks a given amount of a sample from a sample cup into a reaction cup while conveying the sample cup and the reaction cup on two separate conveyers to set off the reaction for determination of a specific component in the sample. However, the structural complexity of an analyzer having two conveyers due to movable parts indispensable to the conveyers makes its maintenance difficult and leads to increase in its production cost and size. Therefore, conveyance of a sample cup and a reaction cup by one conveyer has been suggested.

In biochemical and immunological analyses, it is common to determine more than one specific component in a sample to make good use of samples from examinees and to secure more accurate diagnosis based on multiple components. For such multiple analyses by an analyzer in which sample cups and reaction cups share the same conveyer, a sample cup containing a sample placed at an arbitrary position on the conveyer is followed by as many reaction cups as the measurements to be done with the sample, namely the specific components to be measured in the sample so that the sample and the reaction cups to be used for the analysis of the sample are conveyed successively. If it is necessary to dilute or treat the sample beforehand, a diluent cup or the like is interposed between the sample and the reaction cups behind the sample.

An analyzer sucks a given amount of a sample from a sample cup into a reaction cup on a moving conveyer, if necessary after preliminary dilution or pretreatment of the sample with a reagent, and if necessary adds other reagents, to set off the reaction for determination of a specific component in the sample. Because the sample cup and the reaction cups move on a single track on the same conveyer, the conveyer has to position reaction cups just under the nozzle by making quick motions immediately after a sample is sucked from the sample cup containing it at the same position so that the sample sucked from the sample cup is ejected into the reaction cups behind the sample cup. Therefore, the conveyer has to make quicker motions more frequently to increase the through put speed.

If the motions of the conveyer get quicker and frequent, it is virtually impossible to load additional sample cups or reaction cups on the conveyer while the analyzer is in action, and the conveyer has to be scaled up to accommodate a lot of cups, sacrificing the advantage easiness of downsizing and simplification of such an analyzer. In addition, it is quite difficult to conduct so-called "cut-in" analyses of samples in need of urgent analyses.

The first object of the present invention is to provide an analyzer available in a small size and with simple structure by using a single conveyer which conveys both sample cups and reaction cups intermixedly at a moderate speed which allows loading of additional sample cups or reaction cups on the conveyer in action As described above, an automatic analyzer with a single conveying means such as a conveyer is obtainable in a small size and with light weight and reduced costs, while it is not free from the possibilities that the operator loads sample cups or reaction cups in the wrong places or the wrong reaction cups unsuited to the specific components to be measured by mistake.

Thus, misplacement of sample cups or reaction cups on the conveying means can make it impossible to conduct intended analyses even without causing trouble in the subsequent automatic analyses and can end up with the wrong results because a reaction cup for a specific component is used for a different specific component.

Accordingly, the second object of the present invention is to provide an automatic analyzer which eliminates operational mistakes such as misplacement of sample cups or reaction cups on a conveyer by an operator as mentioned above and even detects, if happen, such operational mistakes.

To attain the above-mentioned first object of the present invention, the present invention provides an analyzer which determines a specific component in a sample while conveying a sample cup containing the sample and a reaction cup containing a reagent which reacts with the sample, which is characterized in that: (1) the analyzer comprises a conveyer which conveys sample cups and reaction cups intermixedly on a closed track, (2) the analyzer comprises a reactor which is equipped with a thermostat which maintains the reaction cups at a predetermined temperature, a trashbin which collects used reaction cups, an up-down nozzle unit which sucks in and out a predetermined amount of a sample and a reaction cup lift which carries a reaction cup between the conveyer, the reactor and the trashbin, (3) the nozzle unit and the reaction cup lift reciprocate on a straight track, driven by different drive units separately or by the same drive unit, (4)

the trashbin is placed on the straight track of the reaction cup lift, (5) at least part of the closed track of the conveyer is straight and overlaps the straight track of the nozzle unit and the reaction cup lift, and (6) the straight part of the track of the conveyer accommodates at least two cups.

To attain the above-mentioned second object of the present invention, the present invention provides an automatic analyzer which determines a specific component in a sample while intermixedly conveying a sample cup containing the sample which present sample identification information which identities the sample in the sample cup and a reaction cup containing a reagent for determination of the specific component in the sample which presents specific component information which identifies the specific component by one conveyer, wherein the automatic analyzer comprises; (1) a storage means which stores test order information including specific component information to identify at least one specific component to be measured for each sample, (2) a first identification means which reads the sample identification information presented by each sample cup, (3) a work list preparing means which selects the specific component information which identifies at least one specific component in the sample to be measured from the test order information stored in the storage means on the basis of the sample identification information for the sample read by the first identification means and prepares a work list consisting of the sample identification information for sample and the specific component information identifying the specific component(s) in the sample to be measured, (4) a loading order determination means which determines the order in which sample cups and reaction cups are loaded on the single conveyer from the work list, (5) a second identification means which automatically reads the specific component information presented by a reaction cup conveyed by the conveyer, and (6) a collating means which compares the specific component information read by the second identification means with the determined order and indicates whether or not they are matched.

The preset invention is applicable to an automatic analyzer which determines specific components by using a different reagent for each or some specific components at least partly prepacked in reaction cups. Such automatic analyzers include, for example, automatics immunological analyzers which determine specific components in samples by using immunological reactions and automatic biochemical analyzers which determine specific components in samples by using biochemical reactions. Now an automatic immunological analyzer embodying the present invention will be described in detail by reference to drawings.

Figure 1:
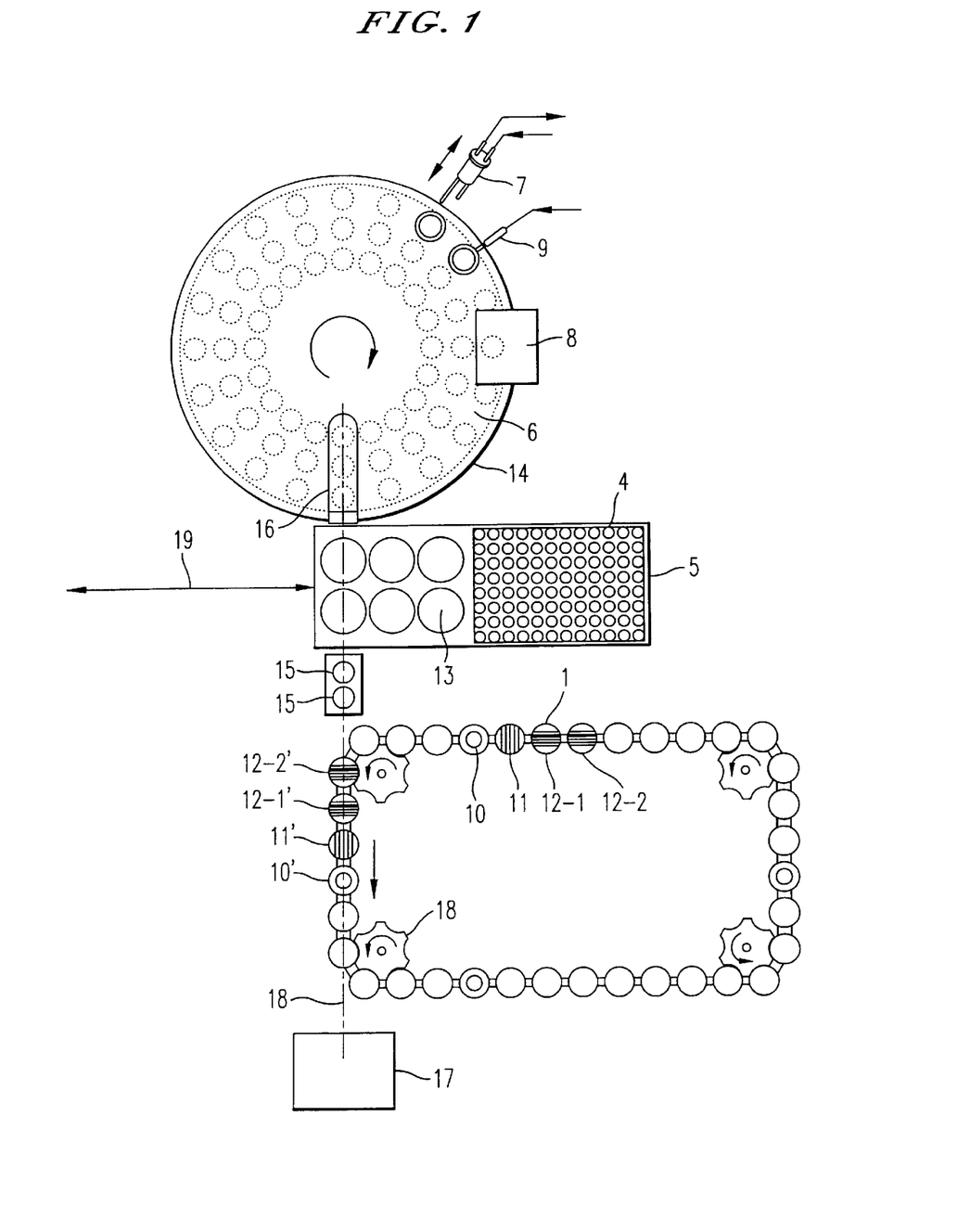
FIG. 1 illustrates one embodiment of the analyzer of the present invention.
Figure 2:
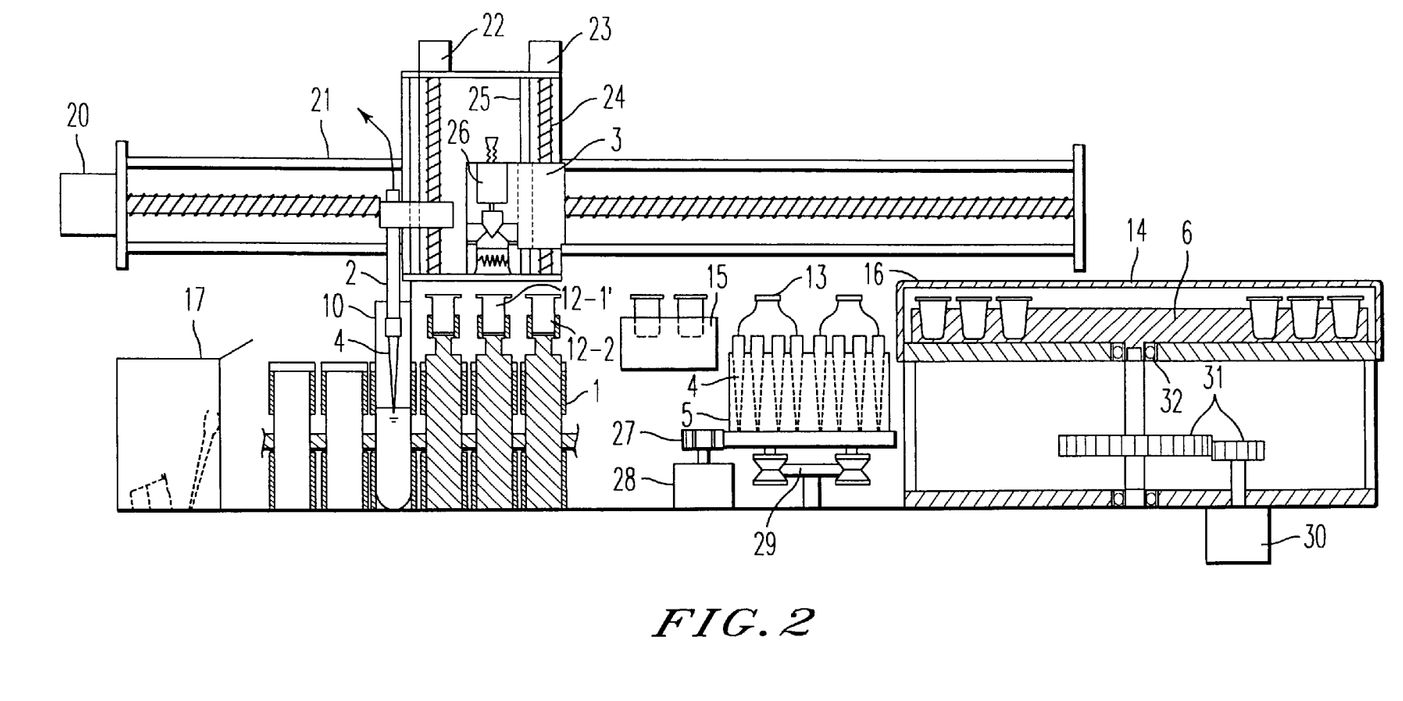
FIG. 2 is a sectional view of the analyzer shown in FIG. 1 (along the reciprocation tracks of the nozzle unit 2 and the reaction cup lift 3).

FIG. 1 and FIG. 2 are top and sectional views of the analyzer according to the first aspect of the present invention.

A sample cup 10 contains a sample in it. As the sample, blood, serum, plasma and urine are used for immunological and biochemical analyzers, and river water and liquid extract from soil may be used as sample for chemical analyzers for environmental analyses. Reaction cups are used to provide space in which reactions of samples and reagents necessary for sample analyses are carried out, and may be empty or prefilled with reagents for determination of components to be measured (hereinafter referred to as "specific components"), depending on the mode of the analysis. For example, biochemical analyzers mix a sample with a chemical reagent which undergoes color-producing biochemical reaction with a specific component in a reaction cup, while immunological analyzers mix a sample with an antigen or an antibody which undergoes an immunological reaction with a specific component in a reaction cup. For analyses of samples which contain a specific component at too high concentrations to measure or need certain pretreatment, dilution cups or pretreatment cups may be used to dilute samples or mix samples with pretreatment reagents in them.

In cases of reaction cups prefilled with a reagent, the reagent may be in a liquid state or a lyophilized state. When reaction cups contain all the reagents necessary for analysis or when empty reaction cups are used, the reagents may be added into reaction cups being conveyed by a conveyer or in the reactor which will be described later. Especially, for immunological analyzers, reaction cups prefilled with such a reagent as mentioned above are available. For example, in determination of a specific substance by heterogeneous one step sandwich EIA, an antibody with binding specificity for the specific substance immobilized on water insoluble magnetic beads and another enzyme-labeled antibody with binding specificity for the specific substance may be prepacked after lyophilization. Reaction cups of this type are available for competitive EIA and assay using a fluorescent or chemiluminescent substance as a label instead of an enzyme as well as sandwich EIA.

The sample cups and reaction cups as above mentioned are loaded on a single conveyer 1 and conveyed on a closed track. The conveyer may be comprised of, for example, an endless track of a conveyer belt or a snake belt, a drive unit such as a sprocket wheel 18 and a support for the endless track, as shown in FIG. 1. In FIG. 1, the sprocket wheel 18 also serves as the support. The sizes and shapes of sample cups and reaction cups and, if any, dilution and pretreatment cups may be the same or different. When their sizes and shapes are different, an adaptor may be used to fit them on the conveyer.

The conveyer 1 conveys sample cups and reaction cups intermixedly on a closed track. The conveyer is preferred to be designed so that every two neighboring cups on the conveyer keep a constant interval between their centers for the reason described later. The automatic analyzer of the preset invention can be reduced in size as compared with analyzers in which these different types of cups are conveyed by their own conveyers. The conveyer is preferably driven intermittently so as to move the same distance as the intervals of the centers of two neighboring cups on it. As shown FIG. 1, a sample cup 10 is followed (or preceded) by a reaction cup 12 containing a reagent proper for a specific component in the sample in the sample cup 10, if present, across a dilution cup 11. Thus, in the analyzer of the present invention, two sample cups are not loaded on the conveyer, not in tandem, so as to interpose at least one reaction cup between them. Not all samples require one dilution cup each, and some samples with no need for dilution require no dilution cups, while samples which need at least two steps of dilution require at least two dilution cups. The same applies to pretreatment cups.

A sample sucked from a sample cup and a reagent, if not prepacked in the reaction cup, are ejected into a reaction cup on the moving conveyer 1, optionally mixed with a solubilizer or other reagents, to set off the intended reaction. Subsequent washing (B/F separation step) by an appropriate method and addition of supplementary reagents are followed by detection of a signal indicating the presence or concentration of the specific substance such as color, fluorescence or luminescence after a certain period of time, and the presence or concentration of the specific substance is determined from the detected signal intensity.

The analyzer of the present invention transports a reaction cup from the conveyer 1 to the reactor 6 in the course of an analysis, to allow the reaction to proceed and detects the signal there. For this purpose, the reactor 6 is furnished with a means for supporting reaction cups described later and various equipments. The reactor is equipped with a thermostat which maintains reaction cups at a predetermined temperature at the least and maintains the temperature so that the intended reaction proceeds effectively in reaction cups transferred thereinto. The thermostat may be constructed, for example, by a combination of a temperature sensor and a heat source. The reactor 6 is preferably designed so as to eliminate factors detrimental to sensitive detection by the detector 8. For example, when the detector is a photometric detector which detects fluorescence or luminescence, the reactor is preferably covered with a shade 14 entirely except for the opening 16 because scattering incident light from the outside can adversely affect the detection sensitivity. The shade over the reactor 6 also has an effect of making the inside temperature of the reactor less susceptible to the outside temperature in addition to the shading effect.

The reactor 6 may be a rotational disk or a caterpillar similar to the conveyer 1 in itself, but preferably a disk with a view to simplifying and downsizing the analyzer because a disc would be able to easily bring any reaction cup right under the opening 16 by rotating in either direction so that an arbitrary reaction cup could be inserted or withdrawn through the opening. The discoid reactor 6 in FIG. 1 has hollow cup holders arranged on three concentric circles so that after a sample and a proper reagent are ejected into a reaction cup, the reaction cup is placed in a hollow cup holder on the innermost or mid circle for a predetermined period, then transferred onto the outermost circle by a reaction cup lift 26 and subjected to washing by a washer 7 and detection by a detector 8 there.

The reactor 6 may be equipped variously depending on the analyzer to which the present invention is applied. For example, in the case of an analyzer for enzyme-labeled heterogeneous immunoassay as described above, around the reactor 6, a magnet shaker (omitted in Figures) which stirs the content of a reaction cup by movement of water insoluble magnetic beads prepacked in the reaction cup, a washer 7 (called a B/F separator) for separation of the labeled antibody not bound to the magnetic beads after the immunological reaction, a dispenser 9 which adds the substrate of the labeling enzyme into a reaction cup and a detector 8 which detects fluorescence, absorbance or luminescence for assay of the activity of the labeling enzyme and the like may be arranged operatively.

Especially, the washer 7 is used for separation of the fraction bound to the water insoluble magnetic beads and the free fraction in the liquid phase and exemplarily has a double pipe structure composed of a washing liquid pipe connected to a washing liquid pressure pomp and a liquid evacuation pipe connected to a vacuum pump via a liquid trap so as to not only eject the wash liquid into a reaction cup but also evacuate the liquid only, leaving the solid phase. Because the water insoluble beads may be beads with diameters from about 1 to 10 nm or fine particles with diameters of submicron to several microns, it is preferred to select the washer structure appropriately according to the shape and size of the beads. Magnetic beads as the water insoluble carrier can be cornered by a magnet in a reaction cup while the washing liquid is sucked out.

In particular, the detector 8 should be selected appropriately according to the signal to be detected. Specifically speaking, for detection of color, fluorescence or luminescence, an absorptiometer, a fluorometer or an emission spectrometer should be selected, respectively. Detection may be done preferably with a reaction solution in a reaction cup in view of simplification and miniaturization of the analyzer, though it may be done with a reaction solution in a detection cuvette. For such a manner of detection, the detector may be so designed as to emit excitation light downward toward a reaction solution and detect the signal from the reaction solution above it (on condition that there is an opening in the shade has). The methodology of detection is classified according to the number of measurements as the one-point detection, the two-point detection based on the difference between two measured values obtained around a given time and the multi-point detection based on the rate of change in the measurement with time obtained from measured values at at least three points of time, and is selected appropriately in view of the mechanism of generation of the signal to be detected, For example, when alkaline phosphatase is used as the label in combination of 4-methylumbelliferyl phosphate as the substrate, since 4-methylumbelliferyl phosphate gives off fluorescence upon dephosphorylation by alkaline phosphatase, the fluorescent intensity is measured at a certain time after addition of the substrate in solution by a fluorometric equipment.

The embodiment shown in FIG. 1 is provided with a dispenser 9 exclusively used for the substrate, though the substrate may be dispensed into each reaction cup by means of the nozzle, because the substrate is added after the immunological reaction and does not participate in the immunological reaction, and such an exclusive equipment can advantageously dispense the substrate into every cup in shorter time in the end.

In ordinary analyses, disposal reaction cups are usually used for the above-mentioned reasons. The analyzer of the present invention carries a reaction cup after an analysis is completed by the detection step from the reactor 6 and dumped in the trashbin 17. For this purpose, the reaction lift is designed to move up and down. The reaction cup lift is used not only when a reaction cup is dumped, but also when a reaction cup is transferred from the conveyer 1 onto the reactor 6 after ejection of a sample and a reagent into it. Holding of a reaction cup may be secured, for example, by providing a hang holder with three claws to the lift with while providing a groove or a flange to be bitten by the claws around the opening of the reactor.

The reaction cup lift is so designed to reciprocate on a straight track connecting the conveyer 1, the reactor 6 and the trashbin 17. Therefore, the closed track of the conveyer 1 should be straight at least partly, and the reaction cup lift should be able to reciprocate on a straight track at least partially overlap the straight track. The reaction cup lift may be lift up and down, for example, by fixing a nozzle to an appropriate pedestal which is driven up and down by a motor via a tangent screw. A motor and a tangent screw may also be used for the reciprocation of the reaction cup lift on the straight track. Because the reaction cup lift 26 picks up or drops off a reaction cup where the reactor 6 crosses the straight track which the reaction cup lift follows to carry it from or to the reactor 6, when the reactor 6 is covered with a shade 14 as mentioned above, the opening 16 of the reactor should be located on the straight track. In a particularly preferable embodiment, part or all of the diameter of the discoid reactor 6 and the opening 16 are arranged on the straight track.

The analyzer of the present invention has an up-down nozzle unit which sucks or ejects a given amount of liquid to suck a sample out of a sample cup into a reaction cup or suck a reagent out of a reagent reservoir into a reaction cup. The nozzle unit may consist of a nozzle and a syringe pump, and the nozzle unit is lifted up and down, for example, by employing such a structure that a nozzle is fixed to an appropriate pedestal which is driven up and down by a motor via a tangent screw.

In the analyzer of the present invention, the nozzle unit is so designed as to reciprocate on a track overlapping the straight part of the closed track of the conveyer. When the nozzle unit in the analyzer of the present invention sucks in a sample or the like with a disposal tip at the end to prevent contamination of samples or reagents, the straight track of the nozzle unit preferably extends to a trashbin in which used tips are dumped. When ejection of a reagent into a reaction cup on the reactor 6 is essential to start the reaction, the straight track of the nozzle unit should extend to the reactor 6. Therefore, in a preferable embodiment, the nozzle unit and the reaction cup lift follow same the straight track.

The nozzle unit and the reaction cup lift may be driven by the same drive unit as shown in FIG. 2 because they reciprocate on the same straight track or overlapping straight tracks, though they may be driven by different drive units.

In the analyzer of the present invention, at least part of the closed track of the conveyer 1 should be straight. For example, the track may be shaped like a rectangle of which one side corresponds to the straight part. Alternatively, the track may be shaped like a ellipse or a circle part of which is straight. The straight part of the closed track of the conveyer should be adjusted to be long enough to accommodate at least two cups. The embodiment shown in FIG. 1 can accommodate six cups on the straight part in total.

The reason why the conveyer should accommodate at least two cups on the straight part is because when a least one specific substance in samples is determined, each sample requires one sample cup and at least one reaction cup. When more than one specific substance in samples has to be determined, the conveyer is preferably so designed to accommodate as many cups as the specific substances to be determined on the straight part. However, if too many specific substances are to be determined, the number of cups is preferably controlled to ten at the maximum by the drive unit for the conveyer so that the analyzer does not become sizable. In the present invention, the conveyer is preferably designed so as to accommodate at least three cups on the straight part in view of additional operations such as dilution and pretreatment.

When the conveyer can accommodate a sample cup and all reaction cups required for the analysis of the sample in the sample cup on the straight part of the closed track, the conveyer is stopped when all the cups are brought on the straight part of the closed track of the conveyer, and the nozzle unit is lifted up and down over the sample cup to suck in the sample, then driven to over the reaction cups by the nozzle unit drive and lifted up and down there to eject the sample into the reaction cups. On the other hand, when the conveyer can not accommodate all these cups on the straight part of the closed track, the suction of the sample from the sample cup and the transfer of the reaction cups to just below the nozzle by the conveyer without moving the nozzle unit are repeated as many times as required, or after a predetermined number of repetitions of the suction and the transfer, the nozzle unit is moved instead of the conveyer so as to eject the reminder in the nozzle. When ejection of a sample into reaction cups entails controlled movements of the conveyer like the latter case, the conveyer preferably moves the same distance as the intervals of the centers of two neighboring cups on it at a time intermittently.

As described above, when all the reagents required for the reaction are not contained in prefilled reaction cups, the reagents which are lacking have to be ejected into the reaction cups additionally. When the analyzer of the present invention requires such an operation, the prefilled reaction cups 13 are located on the straight track on which the nozzle unit reciprocates. When more than one reagent has to be added to the reaction cups, a reagent conveyer may be provided so as to convey the reservoirs for these reagents on a straight track 19 which crosses the straight track for reciprocation of the nozzle unit, preferably at right angles. When the nozzle sucks or ejects the sample or the like with a disposal tip, a tip rack 5 for these tips 4 is placed on the straight track 19 on which the nozzle unit reciprocates. When tip consumption is large, a tip conveyer which supplies new tips may exemplarily be provided so as to move across the straight reciprocation track of the nozzle unit, preferably at right angles, on the straight track 19. In the embodiment shown in FIG. 1, the reagent reservoir 13 and the tip rack 5 are carried by the same conveyer on the straight track in one combination. The tip rack may be a commercially available one that stocks 96 tips at the maximum in a lattice pattern.

Now, the functions of various parts of a immunological analyzer which adopts the present invention will be described. The analyzer uses prefilled reaction cups containing all the reagents necessary for the immunological reaction of a specific substance like those described above.

If dilution of the sample 10' is necessary, the sample and the dilution liquid 13 supplied as a reagent are dispensed by the nozzle unit in a calculated dilution ratio into a dilution cup 11' located behind the sample cup and homogenized. Homogenization is preferably done by sucking the liquid mixture in the dilution cup in and out with the nozzle unit repeatedly in view of simplification of the analyzer, though may be done by providing a vibrator which mechanically vibrates a cup on the conveyer under the conveyer. After homogenization, the nozzle unit sucks a certain amount of the diluted sample and ejects it into reaction cups 12-1' and 12-2'.

Reaction cups containing the appropriately diluted sample are transferred from the conveyer 1 into the reactor 6 maintained at a certain temperature by the reaction cup lift 26. After a certain time of reaction, they are transferred by rotation of the reactor 6 to the washer 7 where the intact fraction which is not bound to the solid phase is removed. After the washing, the reactor 6 rotates to bring the reaction cups to the substrate dispenser which adds the substrate which generates a signal detectable by the detector 8 catalyzed by the labeling enzyme and then rotates again to bring them to the detector 8 which detects the signal. After the detection, the reaction cups are carried by the reaction cup lift and dumped in the trashbin 17. The results of the detection by the detection 8 are put out to a calculator, which is omitted in the Figures.

Some samples need pretreatment before they are subjected to the given reaction. Such a case can be dealt with by controlling the analyzer as in the above-mentioned case of dilution of samples, unless there is a long time lag after sample and a pretreatment reagent are mixed. If a long time lag is needed after the mixing, the conveyer has to be stopped for a long time, and it is not impossible to run an analysis in a short time. Therefore, in the analyzer of the present invention, the sample 10 and the pretreatment liquid 13 supplied as a is reagent are dispensed by the nozzle unit into a pretreatment cup 11' placed behind the sample cup, then the pretreatment cup is carried 6 together with reaction cups by the reaction cup lift 26 to the reactor where the pretreatment reaction takes place. After the pretreatment reaction, the pretreatment cup and the reaction cups are carried to a temporary station 15 on the reciprocation track of the reaction cup lift 26 by the reaction cup lift 26, and the pretreated sample is sucked from the pretreatment cup into the reaction cups by the nozzle unit there. The reaction cups containing the pretreated sample sucked out are carried to the reactor again by the reaction cup lift 26 and treated in the same manner as described above. The temporary station should accommodate at least two cups so that the pretreatment cup and a reaction cup can stay there temporality. The temporary station is provided on the track of the reaction cup lift 3 and may be provided in the reactor 6. The pretreated sample may be dispensed into reaction cups by bringing the respective cups to be handled under the nozzle after the pretreatment reaction in the reactor.

Figure 3:
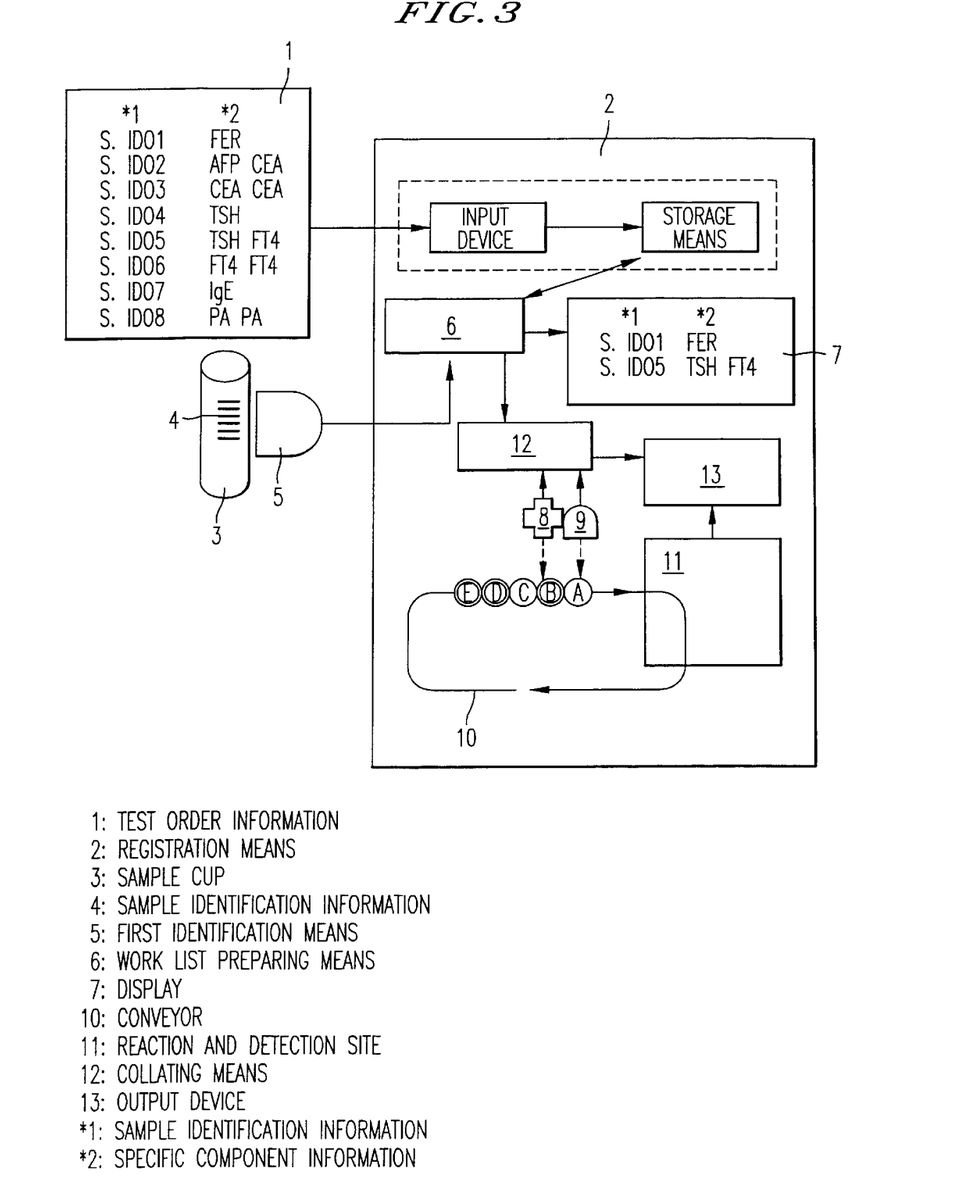
FIG. 3 schematically outlines application of the present invention to an automatic immunological analyzer.
Figure 4:
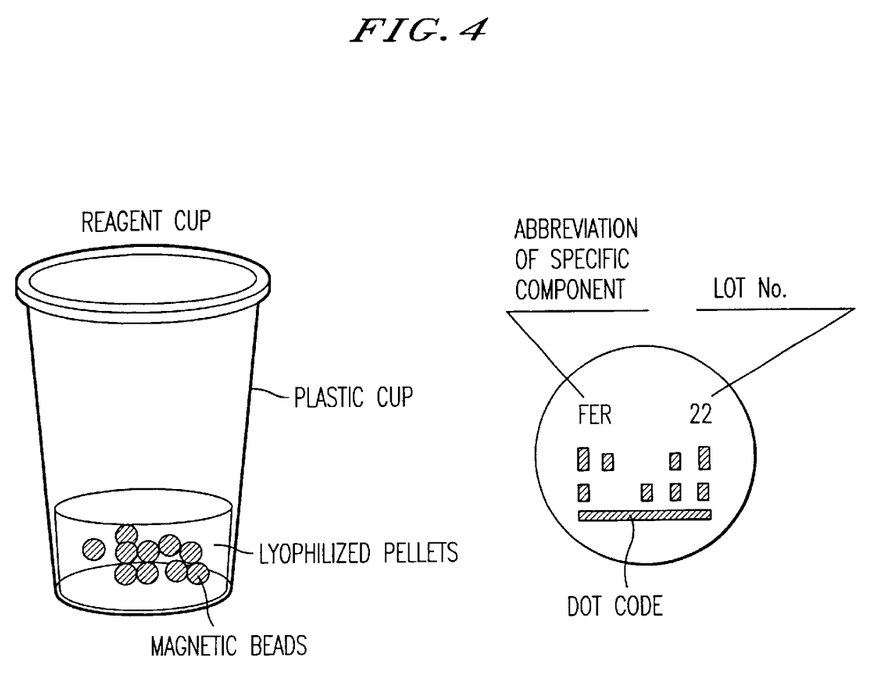
FIG. 4 outlines a reaction cup.

FIG. 3 outlines one embodiment of the automatic analyzer according to the second aspect of the present invention. 1 denotes information on an analysis order, 2 denotes a storage means, 3 denotes a sample cup, 4 denotes a sample code, 5 denotes a first identification means, 6 denotes a work list preparing means, 7 denotes a display, 8 denotes a second identification means, 9 denotes a third identification means, 10 denotes a common conveyer, 11 denotes a reactor and detector, 12 denotes a collating means, and 13 denotes an output device which puts out the results of the analysis. FIG. 4 illustrates a reaction cup.

A sample cup 3 is used to put a sample such as blood, serum, plasma or urine in and carries a sample code on the outer surface such as the lateral surface which enables the first identification means to identify the sample in it. Each sample code has to identify one sample and may consist of English letters, numerals or combination thereof or meaningless patterns but should be assigned individually. Preferable examples of the sample cup in the present invention are a blood collection tube with a sticker carrying a bar code indicating English letters or numerals or such a meaningless pattern as mentioned above in print on the lateral surface or a sample cup carrying a magnetic recording medium on the surface. In the present invention, the sample code is preferred to be visibly identifiable like the above-mentioned code and the like.

The reaction cup is prefilled with reagents necessary for determination of a specific component to be measured, as shown in FIG. 4. As such reagents, chemical reagents which colors by biochemically reacting with the specific component may be mentioned for automatic biochemical analyzers, and antibodies (antigens) which immunologically react with the specific component and enzymes may be mentioned for automatic immunological analyzers.

In the reaction cup shown in FIG. 4, the reagents for heterogeneous one-step sandwich EIA of ferritin, a protein found in blood or serum samples, are contained Specifically speaking, the content of the reaction cup is a lyophilized mixture of an antibody with FER-binding specificity immobilized on water insoluble magnetic beads and another antibody with FER-binding specificity labeled with an enzyme. Reaction cups with such a structure are useful for competitive EIA and immunoassay using a fluorescent or chemiluminescent substance as the label instead of an enzyme in addition to sandwich EIA.

The reagents in a reaction cup may be in a liquid state or a lyophilized state, as mentioned above for FIG. 4. It is possible to put in each sample cup reagents exclusive to the specific component to be measured in the reaction cup beforehand and then add reagents common to all the specific components while the reaction cups are conveyed by a conveyer.

A reaction cup not only keeps the above-mentioned reagents in it but also provides space for reaction of the sample with the reagents, and carries specific component information on the lateral surface or on the tacky foil covering the open top as shown in FIG. 4. Each component code should identify the specific component with which the reagents in the reaction cup is used to react, and may consist of English letters, numerals or combination thereof or meaningless patterns. Preferable examples of the reaction cup in the present invention are a plastic cup with a sticker carrying a bar code indicating English letters or numerals or such a meaningless pattern as mentioned above in print on the lateral surface or a cup carrying a magnetic recording medium on the surface. The reaction cup shown in FIG. 4 containing reagents for FER determination, carries a dot code indicating "FER" together with the letters "FER" and its lot number on the tacky foil covering the open top so that they are visibly identifiably by an operator.

The component information on the reaction cup not only indicates which specific component the reaction cup is used for but also specifies measurement parameters necessary for determination of the component such as the volume of the sample to be used for the determination, the volume of the dilution liquid to be added to the sample, the kinds and amounts of reagents to be added in addition to the reagents prepacked in the reaction cup, the calibration curve to be used at the final stage.

The sample cup and reaction cup as described above are placed on a common conveyer 10 and then carried. The conveyer which carries them may be comprised of, for example, an endless track of a conveyer belt or a snake belt, a drive unit such as a sprocket wheel 18 and a support for the endless track, The conveyer 10 sample cups and reaction cups intermixedly. Therefore, the automatic analyzer of the preset invention can be reduced in size as compared with those having a different conveyer for each type of cups. In the embodiment shown in FIG. 3, a sample cup A is preceded by a reaction cup B containing a reagent for measurement of a specific component in the sample in the sample cup A, and further by a sample cup C and reaction cups D and F containing reagents for measurements of specific components in the sample in the sample cup C. Thus, the analyzer of the present invention places two sample cups on the conveyer, not in tandem, so as to interpose at least one reaction cup between them.

The automatic analyzer of the present invention is furnished with various equipments 11 which encourages the reaction utilized for determination of a specific component such as a biochemical reaction or a immunological reaction or measures the reaction product as the signal of the presence of the specific component. Such equipments may be provided appropriately depending on the type of assay the automatic analyzer of the present invention uses. For example, an automatic immunological analyzer for enzyme-labeled heterogeneous immunoassay may be furnished with an incubator which maintains reaction cups at a given temperature, a pipette which sucks a given amount of samples from sample cups into reaction cups, a magnet shaker which stirs the content of a reaction cup by movement of water insoluble magnetic beads prepacked in the reaction cup, a washer (called a B/F separator) for separation of the labeled antibody not bound to the magnetic beads after the immunological reaction, a dispenser which adds the substrate of the labeling enzyme into a reaction cup, a detector which detects fluorescence, absorbance or luminescence for assay of the activity of the labeling enzyme and a controller which controls the movements of the conveyer and the movements and ejection volume of the pipette. Further, when a reaction cup having an open top covered with a tacky foil is used, a tacky foil breaker which breaks the tacky foil open is provided.

The storage means 2 stores test order information including the above-mentioned sample identification information and specific component information which identifies at least one specific component in a sample to be measured. In the embodiment in the Figure, the test order information 1 includes sample identification information on eight samples expressed by combinations of English letters and numerals (S.ID01, . . . , S.ID08) and specific component information expressed by English letters (FER, AFP and the like) indicating the specific components in each component to be measured. The test order information may include personal information on examinees (such as names, birthdays and gender) and the name of the medical institute in addition to sample identification information and specific component information.

The storage means 2 includes an input device as an interface which inputs sample identification information and specific component information. When a computer in utilized to construct the storage means, a keyboard or a touch panel is connected to the computer to be used as an input device. When a computer in utilized to construct the storage means, the computer may be segregated from the main body of the automatic analyzer of the present invention. As an external computer like this, a host computer for total management of test information at a medical institute may be used.

The first identification means reads the sample identification information on a sample cup and sends the information into the work list preparing means. There is no particular restriction on the first identification means, and for example, it may be a bar code reader when the sample identification information is expressed by a bar code, an optical reader such as a small scanner and a video recorder when the sample identification information is expressed by letters or symbols, or a magnetic reader when the sample identification information is recorded in a magnetic recording medium. The first identification means may be a handy means connected to the automatic analyzer of the present invention or may be constructed by a sample cup carrier provided in a certain place on the analyzer and a means which identifies a sample cup.

The work list preparing means 6 receives the sample identification information read by the first identification means 5, extracts the specific component information on the specific component(s) measured for the sample and prepares a work list including the specific component information indicating the specific component(s) in the sample to be measured. The work list preparing means 6 may includes a display or output device to display or output the resulting work list.

The loading order determination means determines the order in which the operator should load sample cups and reaction cups on the common conveyer on the basis of the work list. The loading order determination means gives instructions about the loading order by displaying the loading order on a display device or outputs the loading order from an output device. The loading order determination means may be omitted if the work list preparing means has the same functions. In FIG. 3, the work list preparing means functions as a loading order determination means as well and not only prepares a work list but only displays the loading order of sample cups and reaction cups on the display 7.

The loading order determination means may determine the order in which sample cups and reaction cups are loaded on the conveyer according to only the order of the sample identification information read by the first identification means reads, but preferably it should calculate the order of samples which leads to the most efficient analysis from all the sample identification information ever read and the specific component information extracted from the storage means based on the sample identification information and determine the order in which sample cups and reaction cups are loaded on the conveyer. For example, the loading order determination means may be a computer so programmed as to appoint reaction cups used for specific components which require dilution of the sample before determination to the end of the loading order of the sample cup containing the sample and the reaction cups used for determination of the specific components in the sample, or appoint the cups used for specific components which do not require dilution of samples to the top of the loading order of cups used for several samples.

The loading order of the reaction cups only among all the cups of which loading order is determined by the loading order determination means, namely the order of the specific components to be measured, is preferably output into a controller which controls the automatic analyzer in whole. This way, the operator does not have to do more than load sample cups and reaction cups on the conveyer by following the instruction on the loading order from the loading order determination means, and the analyzer automatically does measurements and outputs the results. Of course, the controller may control the pipette or the like based on the output from another means which identifies specific component information presented on reaction cups or from a third identification means which will be described later.

Once the cups are loaded on the conveyer in the order determined by the loading order determination means, and the measurements are started, the loaded cups are carried to the respective units as mentioned above in the analyzer by the conveyer. To the automatic analyzer of the present invention, a second identification means 8 is provided near the track of the conveyer to read at least the specific component information presented on reaction cups on the moving conveyer and send it to a collating means 12. The collating means 12 compares the specific component information read by the second identification means with the order determined by the loading order determination means and indicates or outputs whether or not they are matched on a display or from an output device.

There is no particular restriction on the second identification means, and for example, it may be a bar code reader when the sample identification information is expressed by a bar code, an optical reader such as a small scanner and a video recorder when the sample identification information is expressed by letters or symbols, or a magnetic reader when the sample identification information is recorded in a magnetic recording medium. Because the second identification means reads specific component information on reaction cups on the moving conveyed, specific component information should be so located on reaction cups so that the second identification means can read it, for example, on the tacky foil covering the open top of a reaction cup, as shown in FIG. 4. When a reaction cup having an open top covered with a tacky foil is used, the second identification means should be provided ahead of the tacky foil breaker because the tacky foil has to be broken prior to measurement.

In the present invention, in addition to the second identification means, a third identification means 9 is preferably provided near the track of the conveyer to automatically read the sample identification information on sample cups conveyed by the conveyer sequentially, The sample identification information thus read is sent to the collating means 12 sequentially and compared with the loading order of sample cups and reaction cups determined by the loading order determination means and indicates or outputs whether or not they are matched on a display or from an output device.

The collating means 12 may command the controller to stop the measurement, for example, as well as indicates or outputs that the order of reaction cups determined by the loading order determination means and the output from the second identification means are not matched on a display or from an output device, if they are not matched.

For example, if the sample identification information and/or the specific component information includes information which makes them distinguishable, the functions of the second identification means and third identification means can be combined by one identification means. In such a case, the sample identification information on sample cups and the specific component information on reaction cups have to be adjusted at about the same position. However, because sample cups and reaction cups are usually different in shape and size, it is usually difficult to read sample identification information and specific component information by one means. In this case, it is preferred to provide a third identification means in addition to the second identification means. The two identification means preferably read respective information from different directions, for example, sample identification information presented on the lateral side of a sample cup and specific component information presented on the open top of a reaction cup, to avoid mixing up the information read by them.

The automatic analyzer of the present invention having the above-mentioned structure can detect operational errors by man which happen when sample cups and/or reaction cups are loaded on the conveyer. Particularly, cups are preferably loaded on a restricted part of the conveyer so that cups are not loaded on or off downstream from where the second identification means or the third identification means read information.

Now, the automatic analyzer shown in FIG. 3 will be explained from the viewpoint of an operator of the analyzer. The operator exposes a sample cup 3 containing samples to be examined, for example, with sample identification information such as S.ID01 given as a bar codes stuck on it, to a bar code reader as the first identification means 5, and the first identification means 5 reads the sample identification information and sends it to the work list preparing means 6.

The work list preparing means 6 extracts the specific component information (FER) about the specific component to be measured for the sample assigned to the sample identification information S.ID01 from the test order information stored in the storage means 2 and prepares a work list including the sample identification information (S.ID01) an the specific component information (FER). When the storage device is an external computer system, the specific component information relating the sample identification information is communicated between the automatic analyzer and the external computer through an external communication means for preparation of the work list.

In this embodiment, the work list preparing means functions as a loading order determination means too and gives instructions to the operator about the loading order of cups, in this case instructions to load the sample cup carrying the sample identification information S.ID01 first and then a reaction cup carrying specific component information FER, on a display device. The operator places the sample cup carrying the sample identification information S.ID01 at the front position A on the conveyer 10 and then a reaction cup for measurement of FER at the position B behind it, as instructed.

The operator exposes the sample cup 3 containing the next sample to be examined, for example, with sample identification information such as S.ID05 given as a bar codes stuck on it, to the first identification means 5 in the same manner as described above, to have the sample identification information read, and the specific component information TSH and FT4 corresponding to the sample identification information S.ID05 are added to the specific component information FER corresponding to the sample identification information S.ID01 in the work list, on the display device 7 as shown in FIG. 3. The operator places the sample cup carrying the sample identification information S.ID05 at the position C on is the conveyer 10, then a reaction cup for measurement of TSH at the position D and a reaction cup for measurement of FT4 at the position E.

The analyzer of the present invention conveys sample cups and reaction cups intermixedly by a single conveyer and therefore can be simplified structurally as compared with those which convey sample cups and reaction cups by two conveyers separately and is easily available in small size. Further, because it dispenses with a conveyer as one moving part, it requires less frequent maintenance and can be produced at a lower cost. Further, because the conveyer which conveys reaction cups on a closed track does not have to be stopped when a new sample to be analyzed and reaction cups necessary for its analysis are loaded on the conveyer instead of the previous sample which has been already analyzed, the analyzer of the present invention can perform efficient analyses.

Because the reactor is provided separately from the conveyer to adjust reaction cups at a predetermined temperature for the reaction and serve as the detection site as well, and reaction cups are carried between the conveyer and the reactor by the reaction cup lift which reciprocates straight, the reactor and the conveyer in the analyzer of the present invention can have simple structures. Because the trashbin which collects used reaction cups is provided on the straight track of the reaction cup lift, the reaction cup lift is only required to reciprocate on the straight track and move up and down above the straight track and requires just a simply drive unit.

Because the nozzle unit which sucks in and out samples from sample cups is only required to reciprocate on a straight track and move up and down at arbitrary points like the reaction cup lift, the nozzle unit requires only a simple drive unit. Besides, because the straight track of the nozzle unit is covered by (identical to or part of) the straight track of the reaction cup lift, the analyzer can be simplified by combining the drive units for reciprocation of them on these straight tracks.

Because in the analyzer of the present invention, the closed track of the conveyer necessarily has a straight part which accommodates at least two cups and is overlapped by the straight tracks of the nozzle unit and the reaction cup lift so that the nozzle unit and the reaction cup lift reciprocate over the straight part, once the cups required for an analysis are carried to the straight part, the rest of the analysis can be done by moving the nozzle unit and the reaction cup lift back and forth and up and down without moving the conveyer though it depends on the capacity of the straight part.

Thus, the analyzer according the first aspect of the present invention do not require quicker and more frequent motions of the conveyer to do an analysis in a shorter time with improved efficiency, additional sample cups or reaction cups can be easily loaded on the conveyer. Therefore, the analyzer of the present invention can cope with analysis of a large number of samples by loading additional sample cups and reaction cups one after another without increasing the size of the conveyer. Use of the analyzer of the present invention for clinical diagnoses from the necessity of immediate analyses facilitates replacements of sample cups and reaction cups and enables cut-in analyses of urgent samples.

The automatic analyzer according to the second aspect of the present invention which adopts the means (1) to (6) can remove the possibility of diagnostic errors based on the measured values of specific components obtained when the operator has loaded sample cups and reaction cups on the conveyer in the wrong order or used the wrong reaction cups.

By virtue of the storage means, the automatic analyzer of the present invention can check the sample identification information read by the first identification means for read errors. By virtue of the first identification means, the automatic analyzer of the present invention does not require the operator to visually read the sample identification information presented on sample cups or input the information through an input device such as an keyboard and therefore can not only remove read and input errors by the operator but also lighten the operator's work. The work list preparing means and the loading order determination means enable the automatic analyzer of the present invention to lessen the possibility that the operator loads sample cups and reaction cups on the conveyer in the wrong order.

By virtue of the second identification means, and, if present, the third identification means which is preferably provided, the automatic analyzer of the present invention can indicate loading errors made by loading of sample cups or reaction cups in the wrong order by the operator and stop the analysis.

What is claimed is:

1. An automatic analyzer which determines a specific component in a sample while intermixedly conveying a sample cup containing the sample which present sample identification information which identifies the sample in the sample cup and a reaction cup containing a reagent for determination of the specific component in the sample which presents specific component information which identifies the specific component by one conveyer, wherein the automatic analyzer comprises:

(1) a storage means which stores test order information including specific component information to identify at least one specific component to be measured for each sample, (2) a first identification means which reads the sample identification information presented by each sample cup, (3) a work list preparing means which selects the specific component information which identifies at least one specific component in the sample to be measured from the test order information stored in the storage means on the basis of the sample identification information for the sample read by the first identification means and prepares a work list consisting of the sample identification information for sample and the specific component information identifying the specific component(s) in the sample to be measured, (4) a loading order determination means which determines the order in which sample cups and reaction cups are loaded on the single conveyer from the work list, (5) a second identification means which automatically reads the specific component information presented by a reaction cup conveyed by the conveyer, and (6) a collating means which compares the specific component information read by the second identification means with the determined order and indicates whether or not they are matched.

2. The automatic analyzer according to claim 1, wherein the sample identification information presented on a sample cup being conveyed by the conveyer is automatically read by the second identification means or a third identification means, and the collating means compares the specific component information and the sample identification information with the work list.

* * * * *